(12) United States Patent
Wei et al.

(10) Patent No.: US 10,679,417 B2
(45) Date of Patent: Jun. 9, 2020

(54) METHOD AND SYSTEM FOR SURGICAL PLANNING IN A MIXED REALITY ENVIRONMENT

(71) Applicant: EDDA TECHNOLOGY, INC., Princeton, NJ (US)

(72) Inventors: Guo-Qing Wei, Plainsboro, NJ (US); Xiaolan Zeng, Princeton, NJ (US); Xiaonan Zang, Princeton, NJ (US); Li Fan, Belle Mead, NJ (US); Jianzhong Qian, Princeton Junction, NJ (US); Cheng-Chung Liang, West Windsor, NJ (US); Jiahong Dong, Beijing (CN)

(73) Assignee: EDDA TECHNOLOGY, INC., Princeton, NJ (US)

( * ) Notice: Subject to any disclaimer, the term of this patent is extended or adjusted under 35 U.S.C. 154(b) by 0 days.

(21) Appl. No.: 16/045,847

(22) Filed: Jul. 26, 2018

(65) Prior Publication Data
US 2019/0035156 A1    Jan. 31, 2019

Related U.S. Application Data

(60) Provisional application No. 62/538,479, filed on Jul. 28, 2017.

(51) Int. Cl.
*G06T 19/00* (2011.01)
*G06T 7/30* (2017.01)
(Continued)

(52) U.S. Cl.
CPC ............ *G06T 19/006* (2013.01); *A61B 34/10* (2016.02); *A61B 90/36* (2016.02); *G06T 7/11* (2017.01);
(Continued)

(58) Field of Classification Search
None
See application file for complete search history.

(56) References Cited

U.S. PATENT DOCUMENTS

2005/0148848 A1    7/2005  Guang et al.
2006/0093089 A1    5/2006  Vertatschitsch et al.
(Continued)

OTHER PUBLICATIONS

International Search Report and Written Opinion dated Nov. 2, 2018 in International Application PCT/IB2018/055600.
(Continued)

*Primary Examiner* — Sarah Le
(74) *Attorney, Agent, or Firm* — Pillsbury Winthrop Shaw Pittman LLP (57) ABSTRACT

The present teaching relates to method and system for aligning a virtual anatomic model. The method generates a virtual model of an organ of a patient, wherein the virtual model includes at least three virtual markers. A number of virtual spheres equal to a the number of virtual markers are generated, wherein the virtual spheres are disposed on the virtual model of the organ of the patient and associated with the virtual markers. A first position of the virtual spheres and the virtual markers is recorded. The virtual spheres are placed to coincide with physical markers disposed on the patient and a second position of the virtual spheres is recorded. A transformation of the virtual spheres and the virtual markers based on the first and second positions is computed and the virtual model of the organ is aligned with the patient based on the computed transformation.

17 Claims, 6 Drawing Sheets

(51) Int. Cl.
   *A61B 90/00* (2016.01)
   *A61B 34/10* (2016.01)
   *G06T 7/50* (2017.01)
   *G06T 7/11* (2017.01)
   *G06T 7/70* (2017.01)
   *G06T 17/00* (2006.01)
   *G06T 19/20* (2011.01)
   *A61B 34/20* (2016.01)

(52) U.S. Cl.
   CPC .................. *G06T 7/30* (2017.01); *G06T 7/50* (2017.01); *G06T 7/70* (2017.01); *G06T 17/00* (2013.01); *G06T 19/003* (2013.01); *G06T 19/20* (2013.01); *A61B 2034/104* (2016.02); *A61B 2034/105* (2016.02); *A61B 2034/2051* (2016.02); *A61B 2090/363* (2016.02); *A61B 2090/364* (2016.02); *G06T 2207/30204* (2013.01); *G06T 2210/41* (2013.01); *G06T 2219/2004* (2013.01); *G06T 2219/2008* (2013.01); *G06T 2219/2016* (2013.01)

(56) References Cited

U.S. PATENT DOCUMENTS

| | | |
|---|---|---|
| 2011/0295108 A1 | 12/2011 | Cox et al. |
| 2015/0208948 A1 | 7/2015 | Wei et al. |

OTHER PUBLICATIONS

International Preliminary Report on Patentability dated Jan. 28, 2020 in International Application PCT/IB2018/055600.

Fig. 6

METHOD AND SYSTEM FOR SURGICAL PLANNING IN A MIXED REALITY ENVIRONMENT

CROSS-REFERENCE TO RELATED APPLICATIONS

The present application claims priority to U.S. Provisional Patent Application No. 62/538,479, filed Jul. 28, 2017, which is incorporated herein by reference in its entirety.

BACKGROUND OF THE INVENTION

1. Field of the Invention

The present disclosure generally relates to methods and system for computing quantitative information, and aligning virtual patient to real patient in a mixed reality environment in medical applications. Specifically, the present disclosure provides an efficient mechanism for surgical planning in mixed reality environments.

2. Description of Related Art

Recent advances in mixed reality technologies, such as the Microsoft HoloLens, have prompted a wide use of such technologies in medical applications. A three-dimensional (3D) model may be created from patient images, such as CT or MRI images. Such a 3D model may be represented in certain format, for example a Filmbox (FBX) format, and then loaded into an application (i.e., an App) to run in mixed reality devices, such as the Microsoft HoloLens. The 3D model may be viewed in a hologram-like manner in the 3D space from 360 degrees. This may be either used for educational purposes, or overlaid onto the actual patient in a surgery room to help understand the anatomical structure and do surgical planning and guide the surgery.

Currently mixed reality applications only provide viewing functions, with limited user interactions, such as rotation, shift, and zooming of the 3D object models. In medical applications, however, quantitative information is of vital importance. For example, when a donor donates his/her liver, the remnant liver volume has to maintain 30% of the total liver volume. Also in tumor ablation, if there is a vessel of 3 mm diameter or more close to the ablation zone, the heat-sink effect will reduce the effective ablation zone size. In such scenarios, it is important to obtain quantitative information in real-time during surgery, and register and align the mixed-reality 3D anatomy model with the real patient who undergoes surgery so that a mixed reality model can be used to guide a surgical procedure. Therefore, it is highly desirable to provide quantitative information in a registered mixed-reality environment for surgical planning.

SUMMARY

According to an aspect of the present disclosure there is disclosed a method, implemented on a computing device having at least one processor, storage, and a communication platform capable of connecting to a network for aligning a virtual anatomic model. The method includes the steps of generating a virtual model of an organ of a patient, wherein the virtual model includes at least three virtual markers, generating a same number of virtual spheres as the number of virtual markers, the virtual spheres being disposed on the virtual model of the organ of the patient and being associated with the virtual markers, recording a first position of the virtual spheres and the virtual markers placing the virtual spheres to coincide with physical markers disposed on the patient, recording a second position of the virtual spheres, computing a transformation of the virtual spheres and the virtual markers based on the first and second positions; and aligning the virtual model of the organ with the patient based on the computed transformation.

In one example, there is disclosed system for aligning a virtual anatomic model. The system includes an anatomic model generation unit and a registration unit implemented by a processor. The anatomic model generation unit is configured to generate a virtual model of an organ of a patient, wherein the virtual model includes at least three virtual markers. The registration unit is configured to: generate a same number of virtual spheres as the number of virtual markers, the virtual spheres being disposed on the virtual model of the organ of the patient and being associated with the virtual markers, record a first position of the virtual spheres and the virtual markers, place the virtual spheres to coincide with physical markers disposed on the patient, record a second position of the virtual spheres, compute a transformation of the virtual spheres and the virtual markers based on the first and second positions, and align the virtual model of the organ with the patient based on the computed transformation.

By another example, there is disclosed a non-transitory machine readable medium having information recorded thereon for surgical procedure assistance, wherein the information, when read by a machine, causes the machine to perform the steps of: generating a virtual model of an organ of a patient, wherein the virtual model includes at least three virtual markers, generating a same number of virtual spheres as the number of virtual markers, the virtual spheres being disposed on the virtual model of the organ of the patient and being associated with the virtual markers, recording a first position of the virtual spheres and the virtual markers placing the virtual spheres to coincide with physical markers disposed on the patient, recording a second position of the virtual spheres, computing a transformation of the virtual spheres and the virtual markers based on the first and second positions; and aligning the virtual model of the organ with the patient based on the computed transformation.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

The present invention is generally directed to providing quantitative information in a surgical planning process, and for aligning a virtual model to an actual patient in a mixed-reality environment in medical applications.

Figure 1:
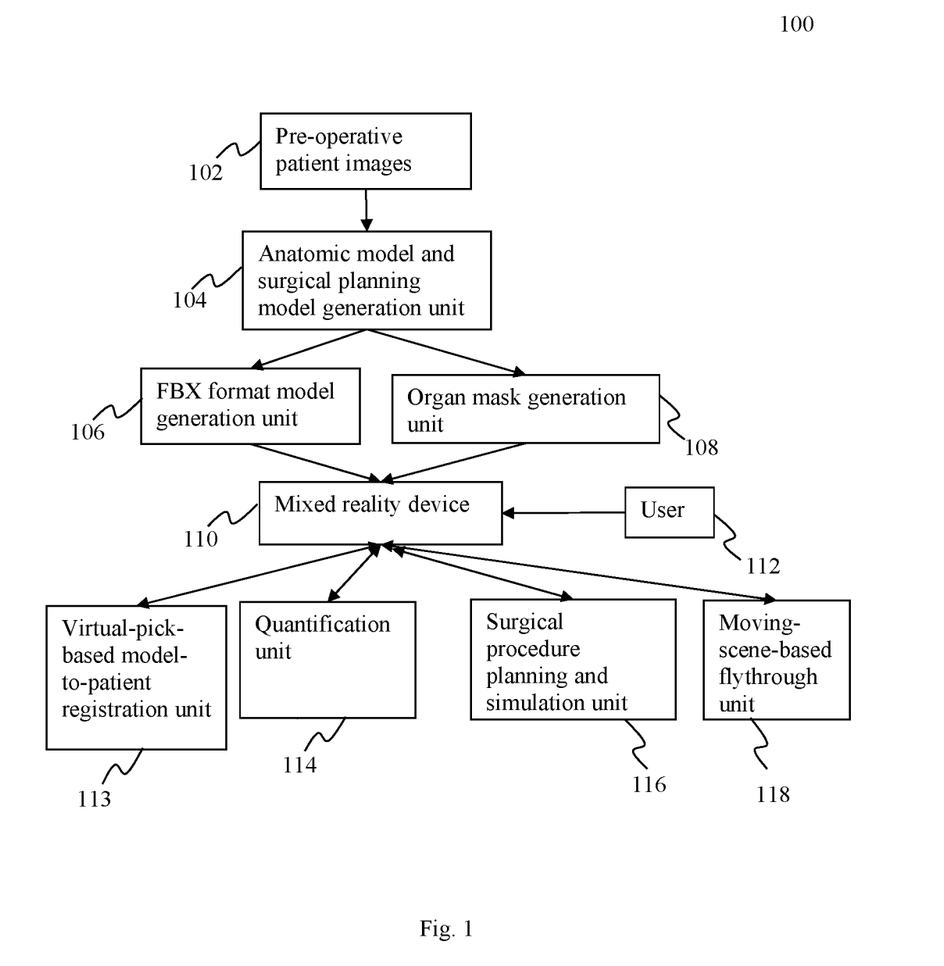
FIG. 1 shows an exemplary system diagram for computing quantitative information and registering virtual model to real patient in mixed reality in accordance with various embodiments.

FIG. 1 shows an exemplary system diagram 100 facilitating the computation of quantitative information, and registration of a virtual model to a real patient in mixed reality, according to an embodiment of the current teaching. The system 100 includes, in one embodiment, a patient anatomic model extraction and surgical planning model generation unit 104, that is generated based on patient's pre-operative images 102, a FBX format generation unit 106, an organ mask generation unit 108, a mixed reality device 110, a mixed reality-to-patient registration unit 113, a quantification unit 114, a surgical procedure planning and simulation unit 116, and a moving-scene-based flythrough unit 118.

The patient anatomic model extraction and surgical planning model generation unit 104 may be configured to segment interested anatomy of the patient from patient images, such as CT or MRI. It may also generate a surgical plan based on the segmented anatomy. The mixed reality format model generation unit 106 may convert the anatomic model and planning model into the mixed reality format, for example a FBX format. The organ mask generation unit 108 may be configured to generate one or more mask file to encode each organ. A user 112 may load the mixed reality format files and mask files into a mixed-reality device 110. The mixed reality-to-patient registration unit 113 may be configured to register the mixed reality environment with the real patient, including scale, size, position, and/or orientation. Thereafter, the mixed reality environment and displays are well aligned with the real patient who undergoes surgery.

The quantification unit 114 may be configured to provide computation of quantitative information regarding the patient organ in the aligned mixed reality environment. The surgical procedure planning and simulation unit 116 may be configured to provide user interaction to plan and simulate surgical procedures in the aligned mixed reality environment. The moving-scene-based flythrough unit 118 may be configured to provide a flythrough simulation inside a selected vascular structure in the aligned mixed reality environment.

The system 100 may further include one or more input devices operated by user 112 such as a computer mouse, a keyboard, a stylus, one or more sensors, 3D manipulation gloves, or any other suitable input device, or any combination thereof. Furthermore, system 100 and/or the input device may also correspond to a standalone device, such as, but not limited to, a mobile device (e.g., a smart phone, tablet, personal digital assistant, laptop, etc.), or a computing device (e.g., desktop computer, camera, etc.). The system may also include one or more processor, memory, communications circuitry, and a display, amongst other features. The processor(s) may include any suitable processing circuitry capable of controlling operations and functionality of the system. In some embodiments, the processor(s) may include a central processing unit ("CPU"), a graphic processing unit ("GPU"), one or more microprocessors, a digital signal processor, or any other type of processor, or any combination thereof. In some embodiments, the functionality of the processor(s) may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, the processor(s) may include their own local memory, which may store program systems, program data, and/or one or more operating systems. However, the processor(s) may run an operating system ("OS"), and/or one or more firmware applications, media applications, and/or applications resident thereon. In some embodiments, the processor(s) may run a local client script for reading and rendering content received from one or more websites. For example, the processor(s) may run a local JavaScript client for rendering HTML or XHTML content.

The memory may include one or more types of storage mediums such as any volatile or non-volatile memory, or any removable or non-removable memory implemented in any suitable manner to store data. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, the memory 304 may be implemented as computer-readable storage media ("CRSM"), which may be any available physical media accessible by the processor(s) to execute one or more instructions stored within the memory.

The communications circuitry may include any circuitry allowing or enabling one or more components of the system to communicate with one another, and/or with one or more additional devices, servers, and/or systems. In some embodiments, the communications circuitry may facilitate communications across a network, such as the Internet. For example, the communications circuitry may access the network(s) using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications. In some embodiments, a web browser using HTTP may be used for communications. Various additional communication protocols may be used to facilitate communications may include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/

TDMA, iDen, LTE or any other suitable cellular network protocol), infrared, BitTorrent, FTP, RTP, RTSP, SSH, and/or VOIP.

The display may, in one embodiment, may be any suitable type of display in communication with one or more of the processor(s), memory, and/or communications circuitry. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen may, in some embodiments, correspond to a display device including capacitive sensing panels capable of recognizing touch inputs thereon. In some embodiments, the display may be an optional component.

Figure 2:
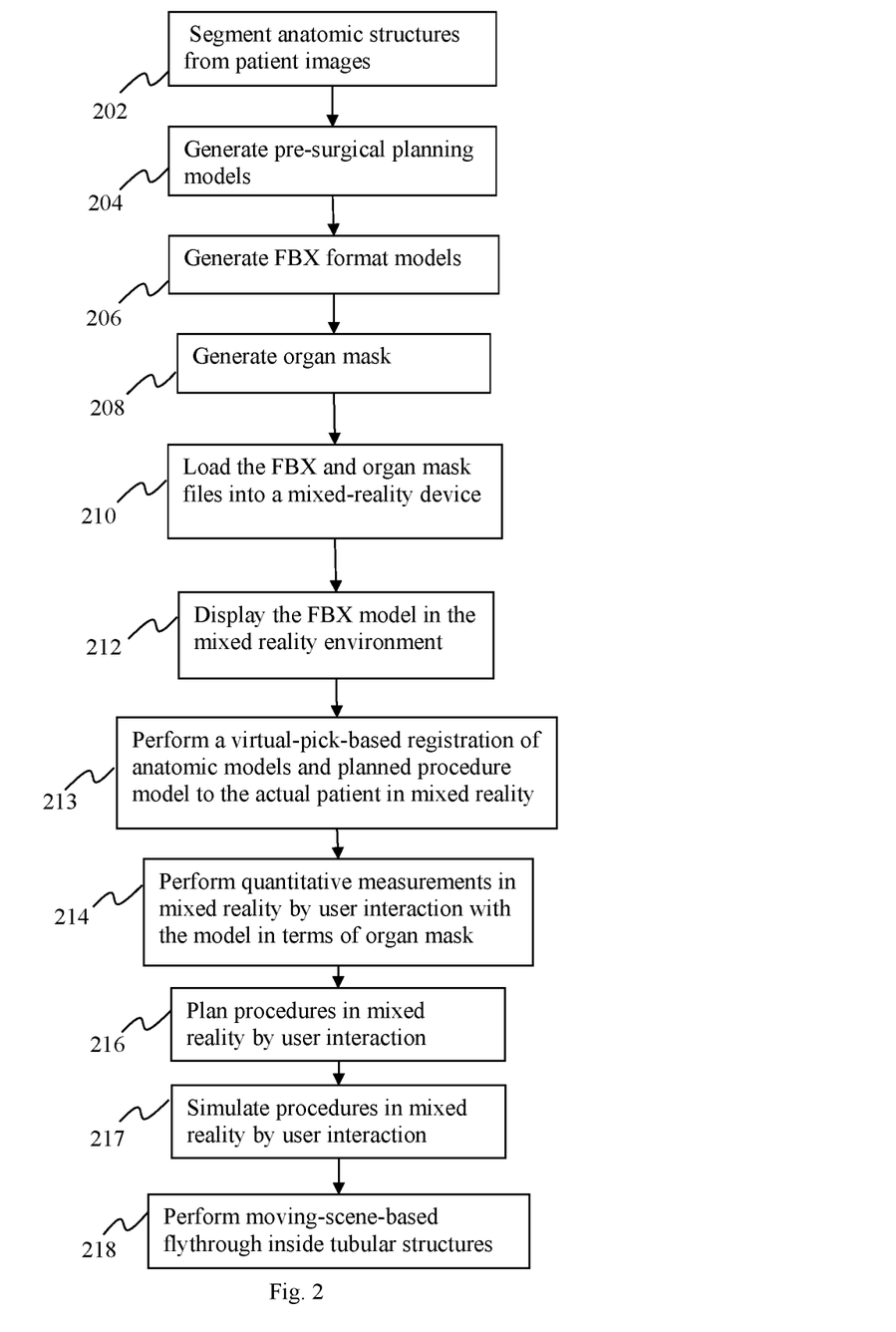
FIG. 2 illustrates an exemplary flow diagram for aligning virtual model to real patient and for providing a quantitative mixed reality in accordance with various embodiments.

FIG. 2 illustrates an exemplary flow diagram for providing a quantitative mixed reality and for aligning a virtual model to a real patient, according to one embodiment of the present teaching. At step 202, patient anatomies of interest may be segmented from patient images. The segmentation may be automatic or semi-automatic. The patient images may be CT or MRI, or any other modalities. From the segmented anatomies, a surgical planning model may be generated at step 204. This may include a lesion resection plan, a transplantation plan, or an interventional plan. Both the patient anatomies and the surgical plans may be converted to a mixed-reality format at step 206. Such a mixed reality format can be FBX or any other format that can be readily loaded into a mixed reality device. At step 208, the segmented anatomy may be encoded to a mask file. For example, an 8-byte per pixel format may be used to encode 8 organs, where each bit is used to represent one organ. In one embodiment, if the bit value is 1, it means that that organ is present at that pixel. Otherwise, the organ is not present in that pixel. At step 210, the mixed-reality format file and the mask file are loaded into a mixed reality device. The mixed-reality format file may be used to display the organs and the surgical plans at step 212, while the mask file may be loaded into the memory of the device, but may not be displayed.

At step 213, the mixed reality environment, including the patient anatomies, surgical plans, together with the simulation scene, may be aligned with the actual patient who undergoes surgery.

At step 214, user interaction may invoke the computation of quantitative information in the aligned mixed reality environment. Users can then manipulate the mixed reality device to measure certain information (e.g., distance, angle, diameter, volume, size etc.), on the real patient with/without reference to the displays of patient anatomy 3D model and the surgical plans. The system may compute certain quantitative information based the organ mask and the alignment of the mixed reality and real patient, and display the desired information in real-time. At step 216, surgical plans may be planned interactively by user. The surgery planning may include, but is not limited to, tumor resection, transplantation, ablation, and biopsy, etc. The planned surgery (e.g. resection surface, needle path, ablation zone, trans-vascular path, etc.), may be displayed on the real patient in the aligned mixed reality environment, with the corresponding quantitative information and warning messages which are desirable by surgeons. Once a surgery plan has been made, at step 217, user can interactively simulate and practice the surgical procedure in the aligned mixed reality environment displayed on the real patient. Comparison of the simulated procedure can be made with the surgical plan.

At step 218, a moving-scene based flythrough may be performed based on a user-selected vascular structure. Different from conventional flythrough, the scene of the model may be made moving to create a flythrough effect.

Figure 3:
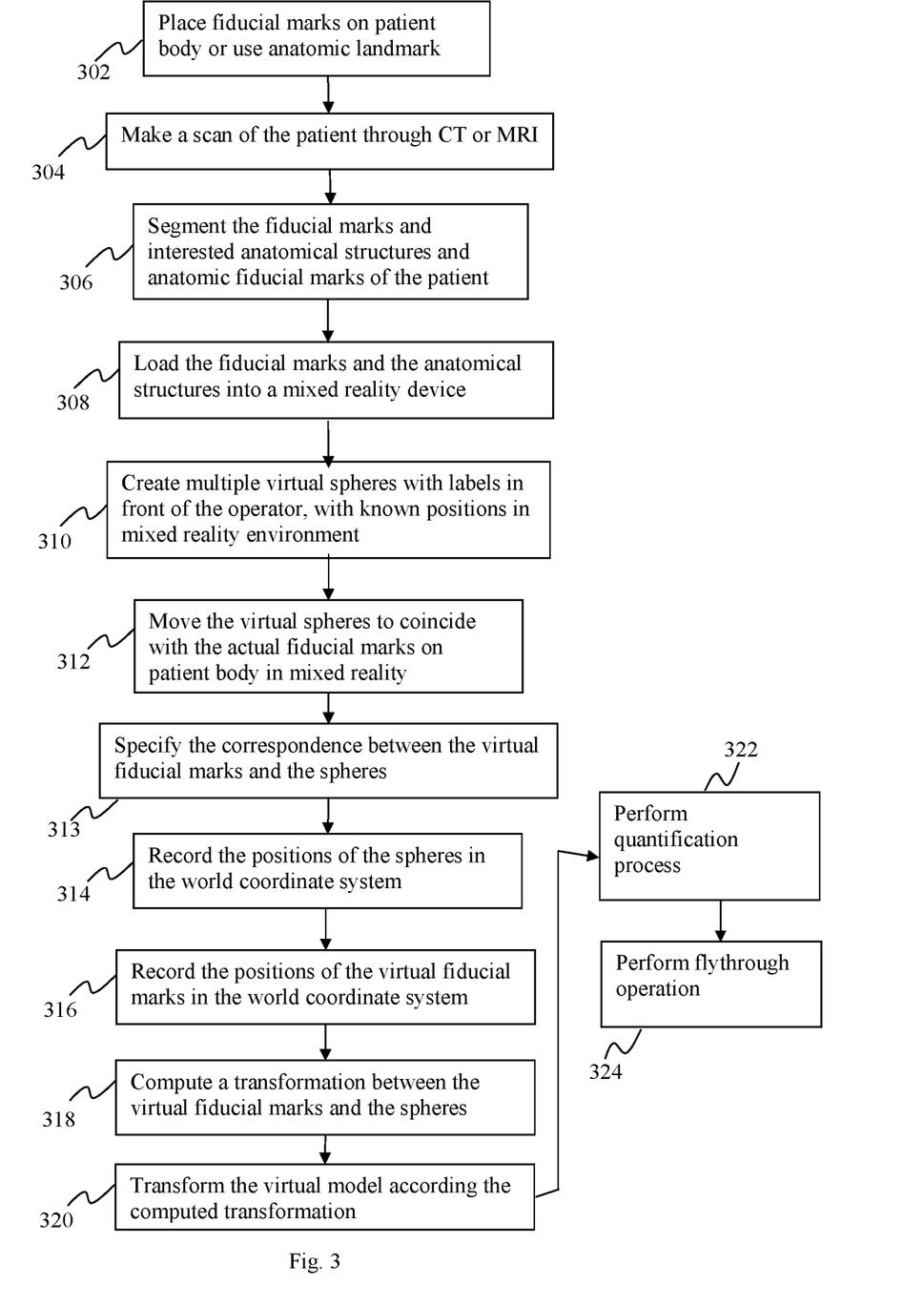
FIG. 3 illustrates an exemplary flow diagram of the virtual-pick-based model-to-patient registration in mixed reality in accordance with various embodiments.

FIG. 3 illustrates an exemplary flow diagram of the virtual-pick-based model-to-patient registration unit 113, according to one embodiment of the present teaching. Specifically, by one embodiment, the model-to-patient registration unit 113 registers a virtual anatomic model to a real patient in a mixed reality environment. To achieve this, multiple fiducial marks may be placed on the patient body, at step 302. Alternatively, anatomic landmarks may be used. In this case, no external fiducial marks may need to be placed on patient body. Anatomic fiducial marks may include, but are not limited to, nipples, belly buttons, and vessel bifurcations (for open surgery). A scan of the patient may be made at step 304. The requirement for the fiducial marks, in one embodiment, is that they can be identified in the patient scans. At step 306, the fiducial marks, together with the anatomic organs (including anatomic fiducial marks), may be segmented from the scanned images, and may be converted to the FBX format and loaded into a mixed reality device at step 308. At step 310, multiple virtual spheres may be generated at known positions in the viewer's coordinate system (i.e., a virtual coordinate system). The spheres may be labeled with different numeric numbers or with distinguishing colors. The user may move the spheres, at step 312, to the same locations as true fiducial marks or anatomic landmarks on patient body. At step 313, correspondence of the spheres with virtual fiducial marks may be specified, based on the distinguishing identity of the spheres (by color or numeric number). The positions of the spheres in the world coordinate system (i.e., the virtual environment) may be then recorded at step 314. The world coordinates (i.e., virtual coordinates) of the virtual fiducial marks may also be recorded at step 316. These coordinates of and the correspondence between the virtual fiducial marks and the virtual spheres may be used to compute a rigid transformation between the model coordinate system and the patient coordinate system, at step 318. The virtual model may then be moved to align with the real patient based on the computed transformation at step 320. It may also be possible that the spheres be placed on a distinguishing surface, e.g., liver surface in open surgery. Then the coordinates of the spheres on the surface may be used to register the same surface in the virtual model to compute the transformation between the virtual model and the real patient. In step 322, a quantification process may be performed on the aligned virtual anatomic model. Thereafter, in step 324, a flythrough effect operation may be performed on a tubular structure of the aligned anatomic model. Details regarding the quantification process (step 322) and the flythrough effect (step 324) are described next with reference to FIGS. 4 and 6, respectively.

The patient alignment method above may be extended in different ways to align different coordinate systems. As an exemplary embodiment, it may be used to align a magnetic tracking system with a mixed reality environment. If the fiducial marks are magnetic sensors, or their positions can be obtained by using a magnetic sensor probe (e.g., by touching it), the coordinates of the fiducial marks in the sensor coordinate system may be used to compute a transformation between the sensor coordinate system and the world coordinate system in the mixed reality. As another exemplary embodiment, the fiducial marks on the patient may be sensed by a robot, either through touching by its end effector, or by cameras in terms of stereo vision. In this way, the coordinate transformation between the robot and the world coordinate system in mixed reality may be computed. The transformation between the mixed reality environment and the third application coordinate system may be used to coordinate and display user actions from the third coordinate system into the mixed reality environment.

Figure 4:
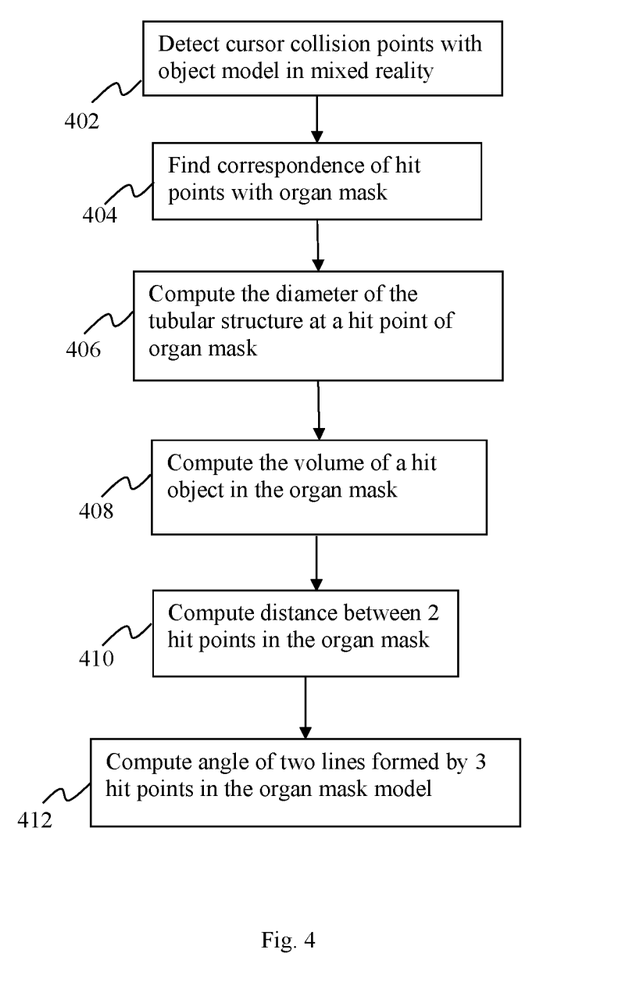
FIG. 4 shows an exemplary flow diagram for providing quantitative information in accordance with various embodiments.

FIG. 4 illustrates an exemplary flow diagram for the quantification unit 114, according to one embodiment of the present teaching. After the virtual model is aligned with the actual patient, a user may tab one or more points on the surface of the virtual anatomy. The surface points may be found by collision detection of the cursor points with the FBX mesh. This is performed at step 402. The surface points may be transformed to find the corresponding points in the encoded mask file at step 404. Different mode of quantifications may be provided for user selection. In the diameter mode, one cursor point may be needed to compute the diameter at the tabbed point of the mask. The diameter of the cross section of the mask orthogonal to the center line of the vascular structure may be computed at step 406. The volume of the anatomy hit by the cursor point may also be computed from the mask file at step 408. In the distance mode, two tabbed points may be used to compute the distance between the points in the mask file, at step 410. Similarly, in the angle mode, at step 412, three tabbed points on the surface may be mapped to the mask to compute the angle between two lines formed by joining the first point and the second point, and joining the second point and third point.

Figure 5:
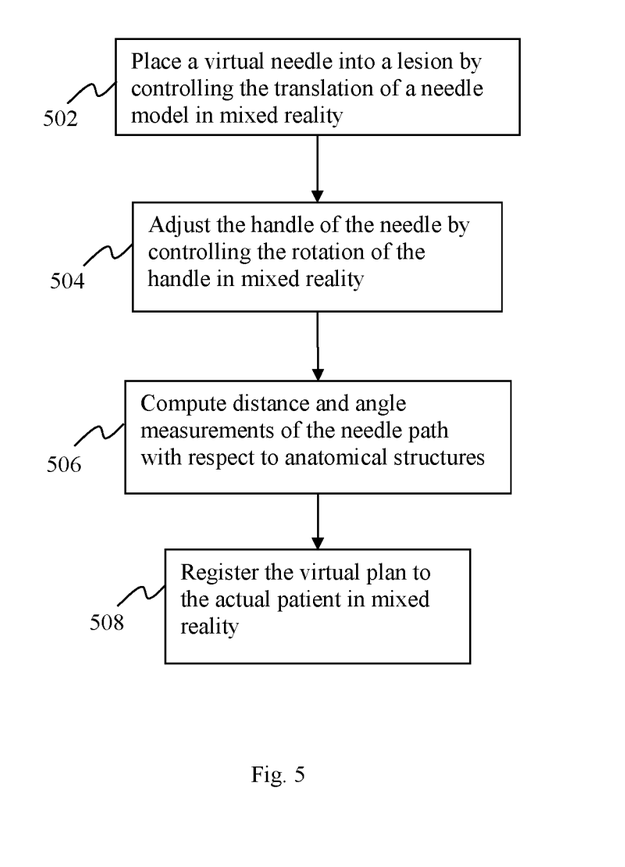
FIG. 5 an exemplary flow diagram of the surgical simulation for interventional procedures in accordance with various embodiments.

FIG. 5 illustrates an exemplary flow diagram of the surgical simulation unit 116 for interventional procedures, according to one embodiment of the present teaching. The below example is based on ablation or biopsy simulation. Other surgical simulations, such as tumor resection or transplantation, may be performed similarly. At step 502, a virtual needle may be placed into a lesion. The tip of the needle may be then fixed and the handle of the needle may be moved to find the appropriate needle path at step 504. While the needle is adjusted, certain quantitative information may be computed in real-time and displayed to the user, at step 506. This may include, but not limited to, the distance between the skin entrance point to the needle tip, the distances from the needle tip to all intersecting organ surfaces, the azimuth and elevation angles of the needle. Since the simulation is performed under the registered mixed reality with the true patient, it may be used to help the surgeons understand the complexities of the procedure.

Figure 6:
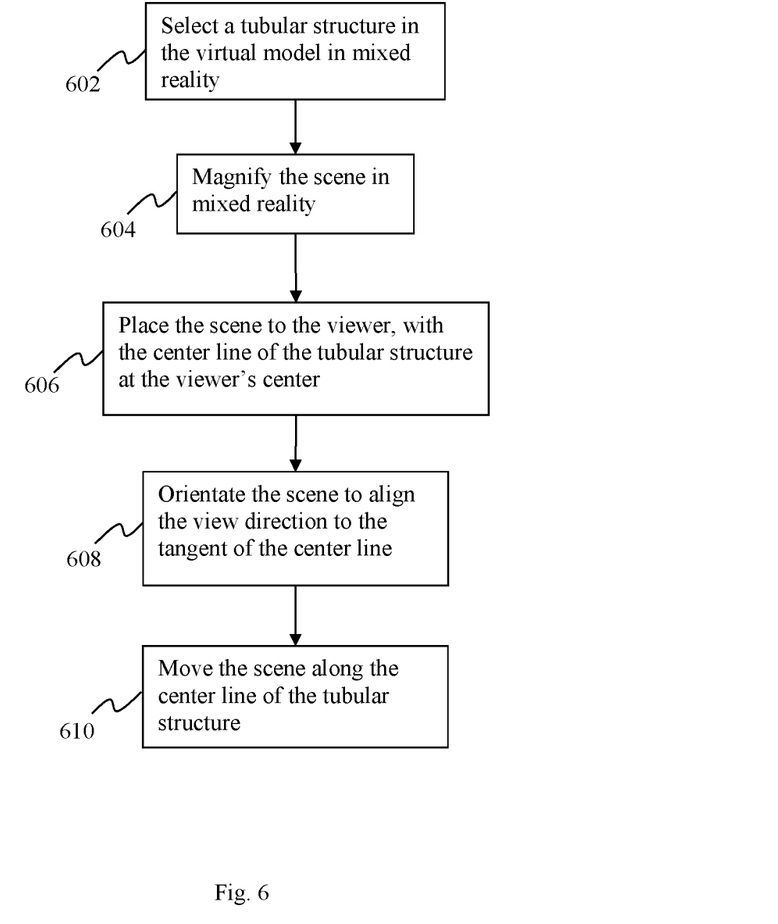
FIG. 6 shows an exemplary flow diagram of the moving-scene-based flythrough in mixed reality in accordance with various embodiments.

FIG. 6 illustrates an exemplary flow diagram of the moving-scene-based flythrough unit 118, according to one embodiment of the present teaching. In conventional flythrough, the viewport (or a virtual camera) may be put inside a vascular (tubular) structure and moves along the center line of the tube. In mixed reality, the view port is the human eye, and it cannot be put inside the tube. Described below is a moving-scene based flythrough method to achieve a fly-through effect. At step 602, a virtual tubular anatomy, such as airway or ureters, may be selected by user for performing the flythrough. At step 604, the virtual model may be magnified, e.g., by a factor of 40. This magnifies the tubular anatomy by the same factor. Additionally, the selected anatomical structure's center line (axis) may be determined, e.g., a center line of a tubular structure (i.e., a line lying on a longitudinal axis of the tubular structure). At step 606, the scene may be placed close to the viewer, such that the center line of the tubular anatomy is the center of the viewer (step 606) and the tangent direction of the center line is aligned with the view direction (step 608). At step 610, scene may be moved toward the viewer along the center line. The flythrough effect may then be created.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. Moreover, it must be appreciated that the steps recited in the flowcharts may be implemented in any order and are in no way limited to the order as depicted in the figures. It is intended by the following claims to claim any and all applications, modifications and variations that fall within the true scope of the present teachings.

What is claimed:

1. A method, implemented on a computing device having at least one processor, storage, and a communication platform capable of connecting to a network for aligning a holographic anatomic model onto a patient, the method comprising:

generating a holographic model of an organ of a patient, wherein the holographic model includes at least three markers;

generating a number of holographic spheres equal to a number of markers, the holographic spheres being disposed on the holographic model of the organ of the patient and being associated with the markers;

recording a first position of the holographic spheres;

placing the holographic spheres to coincide with physical markers disposed on the patient;

recording a second position of the holographic spheres;

computing a transformation of the holographic spheres and the markers based on the first and second positions;

aligning the holographic model of the organ with the patient based on the computed transformation;

magnifying a vessel in the holographic model; and generating a fly-through effect in the magnified vessel by moving a holographic scene including the magnified vessel towards a holographic lens.

2. The method of claim 1, wherein the step of generating the holographic model of the organ of the patient, further comprising:

obtaining a scan of the organ of the patient, the scan including the physical marker disposed on the patient; and segmenting, based on the obtained scan, the physical marker and the organ of the patient.

3. The method of claim 1, further comprising:

placing a virtual needle in a lesion included in the aligned holographic model of the organ;

maneuvering the virtual needle with respect to the lesion; and displaying quantitative information related to at least the virtual needle and the patient.

4. The method of claim 3, wherein the step of maneuvering the virtual needle further comprising:

determining a first portion of the virtual needle that is to be fixed; and moving, based on a user interaction, a second portion of the virtual needle with respect to the first portion.

5. The method of claim 4, wherein the quantitative information includes at least, a first distance between a surface of a skin of the patient and the first portion of the virtual needle, a second distance between the first portion of the virtual needle and other organs of the patient, and an orientation of the virtual needle.

6. The method of claim 4, wherein the first portion of the virtual needle is a tip of the virtual needle and the second portion of the virtual needle is a handle of the virtual needle.

7. The method of claim 1, wherein the holographic model of the organ of a patient and the patient are displayed simultaneously to a user.

8. The method of claim 1, further comprising:
selecting a tubular structure in the holographic model of the organ of the patient;
extracting an axis of the selected tubular structure;
magnifying the selected tubular structure;
moving, towards a user, the holographic tubular structure in a direction along the extracted axis.

9. A system for aligning a holographic anatomic model onto a patient, the system comprising:
an anatomic model generation unit implemented by a processor and configured to generate a holographic model of an organ of a patient, wherein the holographic model includes at least three markers; and
a registration unit implemented by the processor and configured to:
generate a number of holographic spheres equal to a number of markers, the holographic spheres being disposed on the holographic model of the organ of the patient and being associated with the markers,
record a first position of the holographic spheres,
place the holographic spheres to coincide with physical markers disposed on the patient,
record a second position of the holographic spheres,
compute a transformation of the holographic spheres and the markers based on the first and second positions,
align the holographic model of the organ with the patient based on the computed transformation,
magnify a vessel in the holographic model; and
generate a fly-through effect in the magnified vessel by moving a holographic scene including the magnified vessel towards a holographic lens.

10. The system of claim 9, wherein the anatomic model generation unit is further configured to:
obtain a scan of the organ of the patient, the scan including the physical marker disposed on the patient; and
segment, based on the obtained scan, the physical marker and the organ of the patient.

11. The system of claim 9, further comprising:
a surgical planning unit implemented by the processor and configured to:
place a virtual needle in a lesion included in the aligned holographic model of the organ, and
maneuver the virtual needle with respect to the lesion; and
a quantification unit implemented by the processor and configured to display quantitative information related to at least the virtual needle and the patient.

12. The system of claim 11, wherein the surgical planning unit is further configured to:
determine a first portion of the virtual needle that is to be fixed; and
move, based on a user interaction, a second portion of the virtual needle with respect to the first portion.

13. The system of claim 12, wherein the first portion of the virtual needle is a tip of the virtual needle and the second portion of the virtual needle is a handle of the virtual needle.

14. The system of claim 11, wherein the quantitative information includes at least, a first distance between a surface of a skin of the patient and the first portion of the virtual needle, a second distance between the first portion of the virtual needle and other organs of the patient, and an orientation of the virtual needle.

15. The system of claim 9, wherein the holographic model of the organ of a patient and the patient are displayed simultaneously to a user.

16. The system of claim 9, further comprising a moving scene flythrough unit implemented by the processor and configured to:
select a tubular structure in the holographic model of the organ of the patient;
extract an axis of the selected tubular structure;
magnify the selected tubular structure;
move, towards a user, the holographic tubular structure in a direction along the extracted axis.

17. A non-transitory machine readable medium having information recorded thereon for surgical procedure assistance, wherein the information, when read by a machine, causes the machine to perform the steps of:
generating a holographic model of an organ of a patient, wherein the holographic model includes at least three markers;
generating a number of holographic spheres equal to a number of markers, the holographic spheres being disposed on the holographic model of the organ of the patient and being associated with the markers;
recording a first position of the holographic spheres;
placing the holographic spheres to coincide with physical markers disposed on the patient;
recording a second position of the holographic spheres;
computing a transformation of the holographic spheres and the markers based on the first and second positions;
aligning the holographic model of the organ with the patient based on the computed transformation;
magnifying a vessel in the holographic model; and
generating a fly-through effect in the magnified vessel by moving a holographic scene including the magnified vessel towards a holographic lens.

* * * * *